US00PP30561P3

(12) United States Plant Patent
van Rijn

(10) Patent No.: US PP30,561 P3
(45) Date of Patent: Jun. 4, 2019

(54) ***ANTHURIUM* PLANT NAMED 'ARAANTRED5'**

(50) Latin Name: ***Anthurium andraeanum* Linden ex Andre**
Varietal Denomination: ARAANTRED5

(71) Applicant: J&D Horticulture B.V., De Lier (NL)

(72) Inventor: Silvia van Rijn, De Lier (NL)

(73) Assignee: J&D Horticulture B.V., De Lier (NL)

( * ) Notice: Subject to any disclaimer, the term of this patent is extended or adjusted under 35 U.S.C. 154(b) by 0 days.

(21) Appl. No.: 15/732,573

(22) Filed: Nov. 29, 2017

(65) Prior Publication Data

US 2018/0153079 P1 May 31, 2018

(30) Foreign Application Priority Data

Nov. 30, 2016 (QZ) ..... PBR 2016/2991

(51) Int. Cl.
*A01H 5/02* (2018.01)

(52) U.S. Cl.
USPC ..... Plt./369
CPC ..... *A01H 5/02* (2013.01)

(58) Field of Classification Search
USPC ..... Plt./369
CPC ..... A01H 5/02
See application file for complete search history.

(56) References Cited

FOREIGN PATENT DOCUMENTS

EM 20/162991 11/2016

*Primary Examiner* — Keith O. Robinson
(74) *Attorney, Agent, or Firm* — Samuel R. McCoy, Jr.

(57) ABSTRACT

'ARAANTRED5' is a new and distinctive variety of *Anthurium* plant which is characterized by the combination of a compact growth habit with an abundance of foliage and inflorescences, relatively small, durable leaves which are dark green and glossy, large, durable spathes with a broad cordate shape and a vibrant red general coloration, and the stability of all characteristics from generation to generation. The new variety is typically produced as an indoor ornamental plant.

3 Drawing Sheets

Latin name of the genus and species: The Latin name of the genus and species of the novel variety disclosed herein is *Anthurium andraeanum* Linden ex Andre.

Variety denomination: The inventive variety of *Anthurium* disclosed herein has been given the variety denomination 'ARAANTRED5'.

CROSS REFERENCE TO RELATED APPLICATIONS

This application claims priority to the Community Plant Variety Rights application number 2016/2991, filed Nov. 30, 2016, which is herein incorporated by reference.

BACKGROUND OF THE INVENTION

Parentage: The new cultivar is a seedling selection which resulted from the controlled pollination of *Anthurium andraeanum* 'K25' (not patented), the seed parent, and *Anthurium andraeanum* 'K20' (not patented), the pollen parent. Both parents are developed and owned by the inventor and were never commercially released. Said cross was performed by the inventor in De Lier, The Netherlands, in November of 2013. Seeds were harvested from 'K25', sown, and grown to maturity in order to evaluate for unique characteristics which may be of commercial value. In February of 2015, after evaluating the seedlings for approximately one year, one progeny was observed to exhibit durable foliage and durable large, bright red spathes. In March of 2015, after further evaluation to confirm the unique characteristics, the new cultivar was selected for commercialization and given the breeder denomination 'ARAANTRED5'.

Asexual Reproduction: Asexual reproduction of 'ARAANTRED5', by way of meristematic tissue culture, was first performed in March of 2015 at a laboratory in De Lier, the Netherlands. Four successive generations so produced have shown that the unique features of the instant cultivar are stable and reproduced true to type.

SUMMARY OF THE INVENTION

The cultivar 'ARAANTRED5' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Anthurium* cultivar 'ARAANTRED5'. These traits, in combination, distinguish 'ARAANTRED5' as a new and distinct cultivar.

1. *Anthurium* 'ARAANTRED5' exhibits a compact growth habit with an abundance of foliage and inflorescences held at or slightly above the floral plane; and
2. *Anthurium* 'ARAANTRED5' exhibits relatively small, durable leaves which are dark green and glossy; and
3. *Anthurium* 'ARAANTRED5' exhibits large, durable spathes with a broad cordate shape and a vibrant red general coloration.

Figure 1:
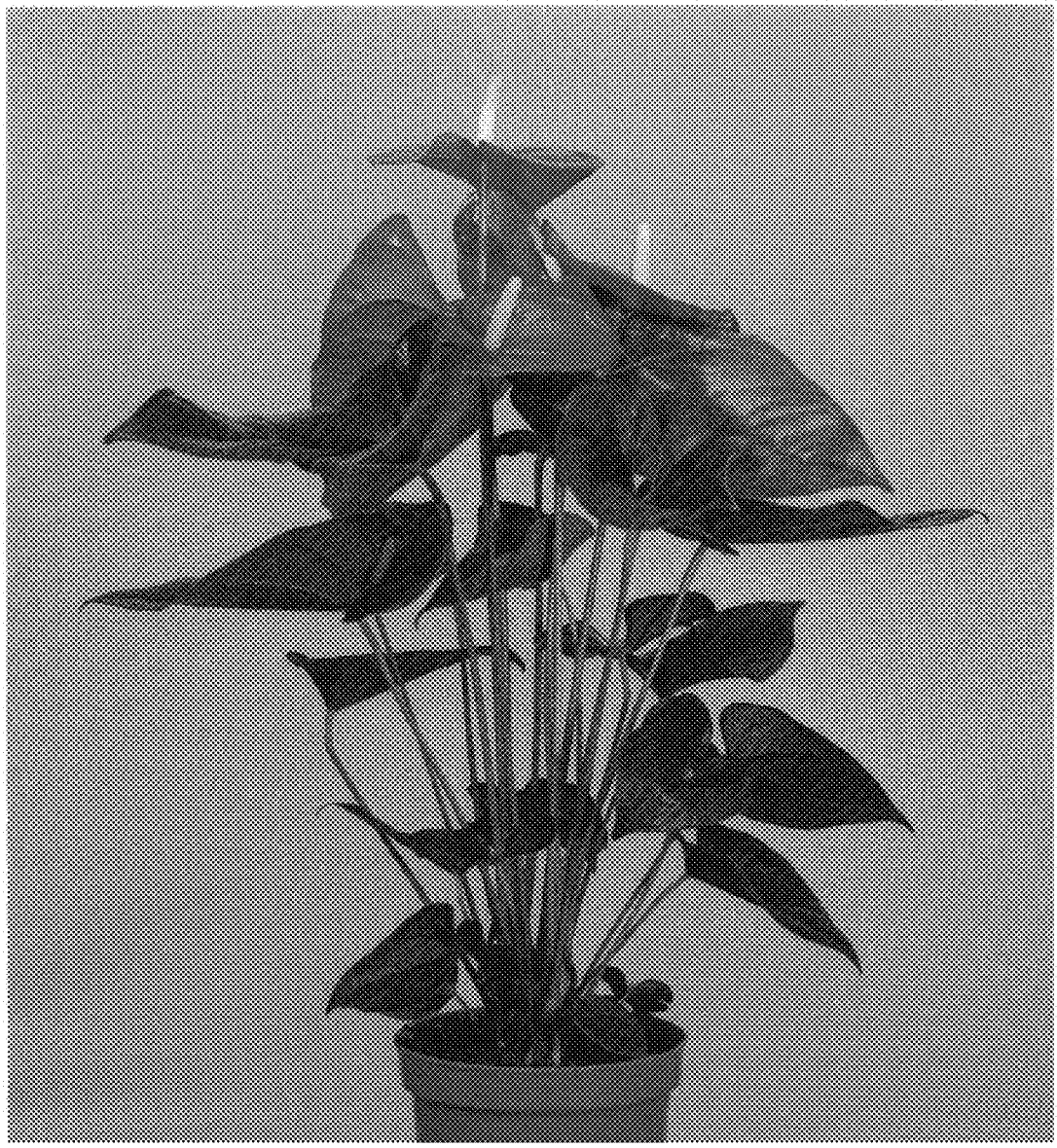
FIG. 1 shows, as nearly true as it is reasonably possible to make the same in color illustrations of this type, an exemplary plant of 'ARAANTRED5', grown in a greenhouse in De Lier, the Netherlands. The plant shown is approximately 9 month old from a rooted cutting, potted into a 15 cm nursery pot.
Figure 2:
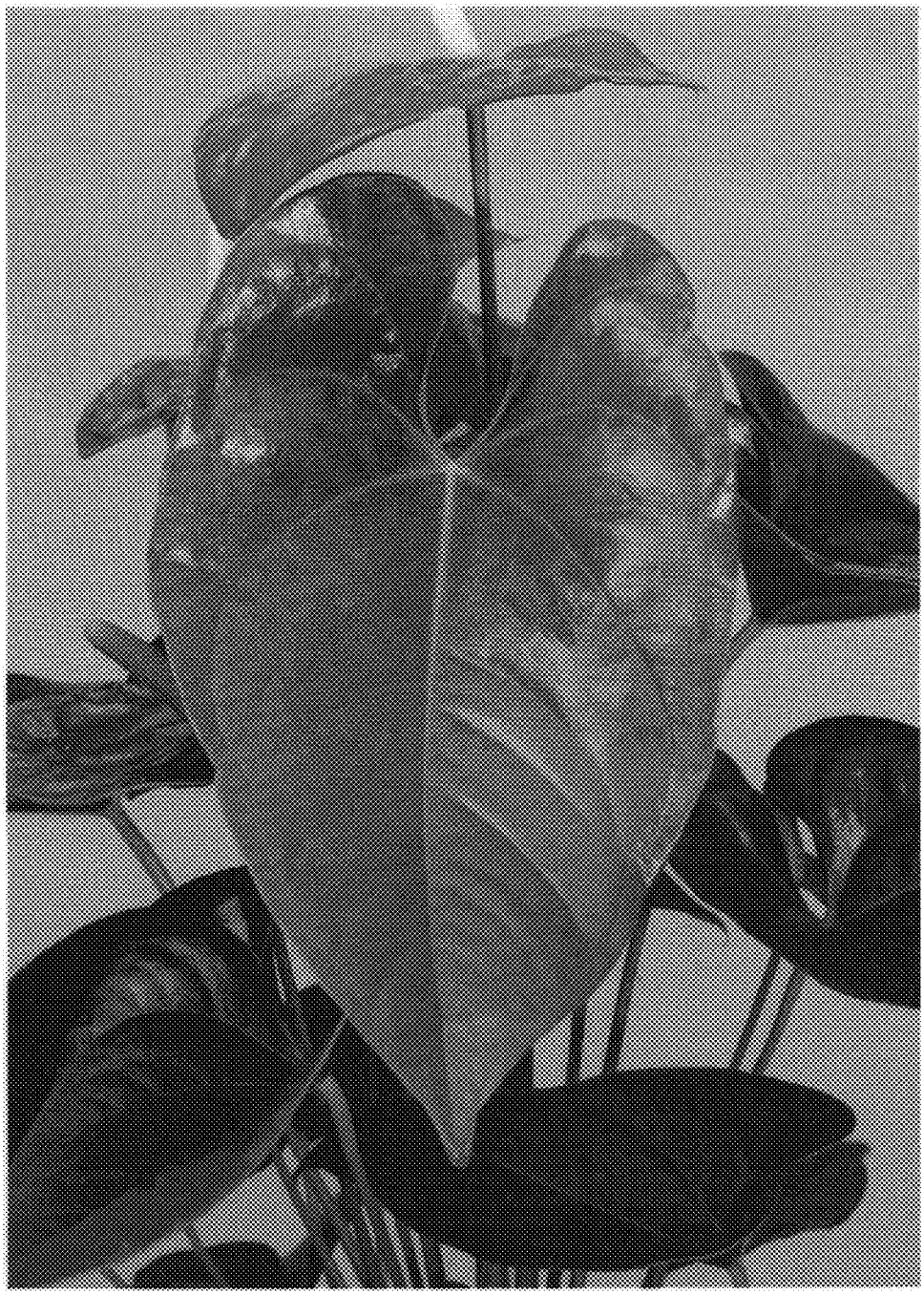
FIG. 2 shows, as nearly true as it is reasonably possible to make the same in color illustrations of this type, the typical foliage of 'ARAANTRED5'.
Figure 3:
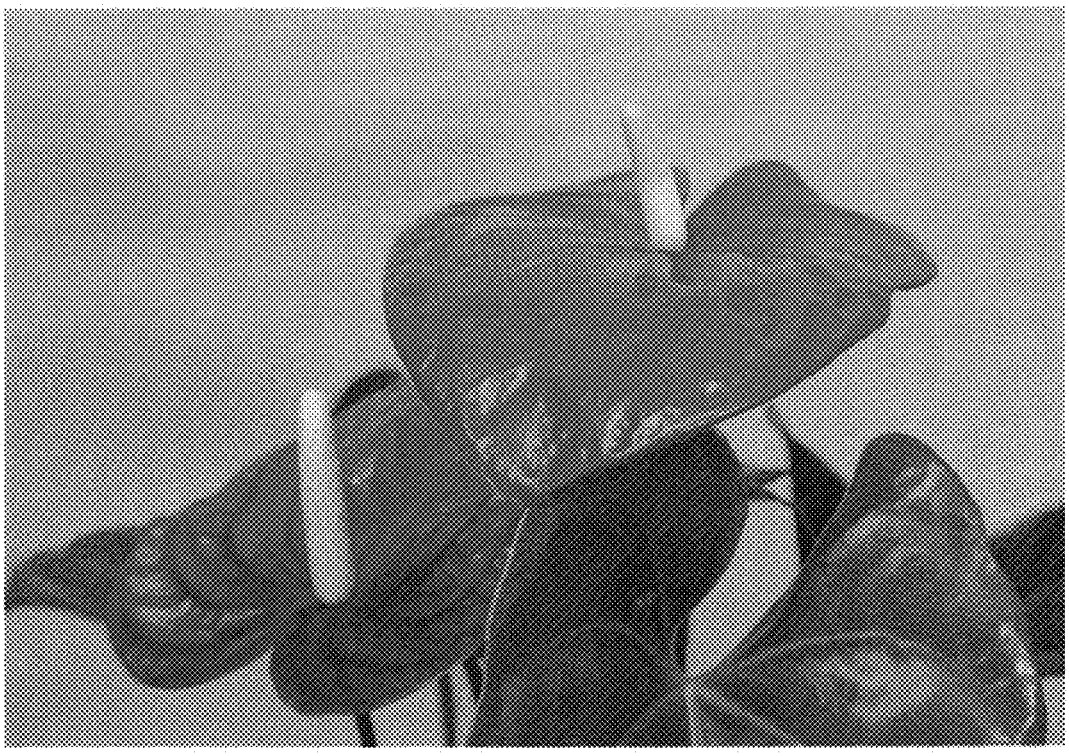
FIG. 3 shows, as nearly true as it is reasonably possible to make the same in color illustrations of this type, the typical inflorescence of 'ARAANTRED5'.

The photographs were taken using conventional techniques and although colors may appear different from actual colors due to light reflectance it is as accurate as possible by conventional photographic techniques.

BOTANICAL DESCRIPTION OF THE PLANT

The following is a detailed botanical description of a new and distinct variety of *Anthurium* known as 'ARAANTRED5', based upon observations made from a sample set of plants grown in 17 cm nursery pots which were approximately 10 month old from a rooted cutting. Plants were grown in a greenhouse in De Lier, The Netherlands, utilizing conventional greenhouse production protocols for *Anthurium*, which consisted of regular irrigation by way of ebb and flood watering benches and fertilizer applications of a complete fertilizer with micro nutrients at an electrical conductivity value ranging from 1.0 to 1.8. No chemical pest or disease measures were utilized in production. Young plants are assimilated to the greenhouse under shade cloth and later move to light levels ranging from 3000 to 4000 lux for the final 5 months of production. Observation data was recorded in October of 2017.

Those skilled in the art will appreciate that certain characteristics will vary with older or, conversely, with younger plants. 'ARAANTRED5' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, sixth edition (2015).

A botanical description of 'ARAANTRED5' and comparisons with the parents and the most similar variety of common knowledge are provided below.

General plant description:

*Growth rate*.—Moderately fast.

*Plant vigor*.—Moderately vigorous.

*Growth habit*.—Dioecious clump-forming, herbaceous perennial; broad upright.

*Plant shape*.—Broad obovate.

*Height*.—49.0 cm in height, to the highest leaf; 55.1 cm to top of the floral plane.

*Width*.—Average 57.5 cm in width.

*Propagation*.—Stem cuttings and meristematic tissue culture.

*Time to initiate roots*.—Approximately 30 days to initiate roots at approximately 23 degrees Centigrade.

*Time to produce a finished marketable plant*.—Approximately 60 weeks to produce a marketable plant in a 14 cm nursery pot.

*Environmental tolerances*.—Adapt to, at least, USDA Zones 10 to 13 and temperatures ranging from as high as 40 degrees Celsius and as low as 5 degrees Celsius; moderate to high tolerance to rain; low tolerance to wind.

*Pest resistance and susceptibility*.—Plants have not been observed to be susceptible or resistant to pathogens and pests common to *Anthurium*.

Root system:

*Root structure; texture*.—Not very dense; non-fibrous; moderately fleshy.

*Dimensions*.—Average length of 14.0 cm long and 0.3 cm in diameter.

*Color*.—Orange-red, nearest to a combination of RHS 35C and 35D.

Stems:

*Branching characteristics*.—Basally-branched plant with leaves growing in small clumps which form short lateral branches.

*Quantity of clumps per plant*.—3.

*Quantity of additional clumps per year*.—3.

*Lateral branches*.—Dimensions — 3.2 cm long and 1.2 cm in diameter. Attitude — Approximately 10 degrees from vertical. Cross-section — Round. Texture and luster — Smooth, glabrous, and moderately glossy. Strength — Strong. Color, juvenile — Yellow-green, nearest to RHS 145C. Color, mature — Green, nearest to RHS 143B. Color at internodes — Green, nearest to RHS 143B.

Foliage:

*Arrangement*.—Alternate.

*Division*.—Simple.

*Quantity of leaves per lateral branch*.—5 leaves per clump.

*Leaf shape*.—Cordate.

*Leaf apex*.—Apiculate; curved downward.

*Leaf base*.—Deeply cordate; basal lobes free to touching.

*Aspect*.—Moderately concave.

*Leaf length*.—Average 22.8 cm in length.

*Leaf width*.—Average 13.8 cm in width.

*Leaf margin*.—Entire; slightly undulate; no lateral lobes present.

*Texture and luster, adaxial surface*.—Smooth, glabrous and glossy.

*Texture and luster, abaxial surface*.—Smooth, glabrous and glossy.

*Juvenile color, adaxial surface*.—Nearest to in between green, RHS 143A, and yellow-green, RHS 144A.

*Juvenile color, abaxial surface*.—Yellow-green, nearest to in between RHS 144A and 146B.

*Mature color, adaxial surface*.—Nearest to in between green, RHS 139A, and yellow-green, RHS 147A, but darker.

*Mature color, abaxial surface*.—Yellow-green, nearest to in between RHS 146A and 146B.

*Venation*.—Vein pattern — Pinnate. Vein color, adaxial surface — Yellow-green, nearest to RHS 144A. Vein color, abaxial surface — Yellow-green, nearest to RHS 145A.

*Petiole*.—Length — 30.3 cm, including the geniculum. Width — 0.4 cm. Texture and luster, both surfaces — Smooth, glabrous and moderately glossy. Color, adaxial surface — Nearest to in between green, RHS 143A, and yellow-green, RHS 144A. Color, abaxial surface — Yellow-green, nearest to RHS 144A. Strength — Very strong. Geniculum — Length — Approximately 2.5 cm. Width — Approximately 0.5 cm. Color — Yellow-green, nearest to RHS 144B. Petiole wings — Length — Approximately 3.2 cm. Width — Approximately 0.5 cm. Color — Yellow-green, nearest to RHS 144C. Stipule — Occurrence — A dry stipule is present at the base of each petiole. Shape — Narrow oblong. Apex — Narrow apiculate to caudate. Base — Broad cuneate. Dimensions — 6.2 cm long and 0.8 cm wide. Texture and luster, both surfaces — Smooth, glabrous, and matte. Color, both surfaces — Greyed-orange, nearest to in between RHS 165A and 166B.

Inflorescence:

*Type*.—Consisting of a spathe and spadix.

*Arrangement*.—Inflorescences are carried at or slightly above the leaf plane.

*Quantity per clump*.—3.

*Quantity per plant*.—8.

*Natural flowering season*.—Winter into spring.

*Height of spathe*.—6.1 cm.

*Time to flowering*.—13 weeks.

*Fragrance*.—Non fragrant.

*Self-cleaning or persistent*.—Persistent.

*Flower longevity*.—Flowers stay in good condition for approximately 4 weeks.

*Peduncle*.—Cross-section — Elliptical. Attitude — Approximately 20 degrees to the lateral branch axis. Length — Approximately 39.9 cm. Diameter — Approximately 0.5 cm. Texture and luster, both surfaces — Smooth, glabrous, and moderately glossy. Color — Yellow-green, nearest to RHS 144A. Strength — Strong.

Spathe:

*Attitude*.—Approximately 15 degrees to horizontal; apex pointed horizontal.

*Length*.—Approximately 14.0 cm.

*Width*.—Approximately 11.5 cm.

*Shape*.—Broad cordate; basal lobes free to touching.

*Aspect*.—Flat to slightly concave to slightly convex; margins at the base are revolute.

*Margin*.—Entire; lightly undulated.

*Apex*.—Apiculate with a mucronate tip.

*Base*.—Cordate.

*Texture and luster, upper surface*.—Moderately rugose, glabrous, and very glossy.

*Texture and luster, lower surface*.—Rugose, glabrous, and very glossy.

*Color*.—Upper surface, when opening — Red, nearest to RHS 45B. Lower surface, when opening — Red, nearest to in between RHS 47B and 47C, and darker towards the apex, nearest to RHS N46B. Upper surface, when fully opened — Red, nearest to RHS 45B, and darker towards the base, nearest to RHS N45A; suffused with yellow-green, nearest to in between RHS 152A and 152B; outer tip is yellow-green, nearest to RHS N144A. Lower surface, when fully opened — Red, nearest to RHS 51A, and fading lighter towards the base, nearest to RHS 51B; outer tip is yellow-green, nearest to RHS N144B. Venation on the upper surface, when fully opened — Greyed-red, nearest to RHS 187A. Venation on the lower surface, when fully opened — Greyed-green, nearest to RHS 197C. Upper surface when fading — Greyed-purple, nearest to RHS 187A; lightly suffused with red, nearest to RHS 53A. Lower surface when fading — Red, nearest to RHS 51A, and fading lighter towards the base, nearest to RHS 51B; outer tip is yellow-green, nearest to RHS N144B.

Spadix:

*Attitude*.—Approximately 65 degrees to the spathe.

*Aspect*.—Straight to weakly incurved.

*Shape*.—Cylindrical.

*Apex*.—Obtuse.

*Base*.—Obtuse.

*Length*.—Approximately 5.3 cm.

*Width*.—Approximately 1.0 cm.

*Texture and luster*.—Smooth, glabrous, and matte.

*Color*.—When opening — Yellow, nearest to RHS 13C. When fully opened — Yellow-orange, nearest to RHS 14D. When fading — Green, nearest to RHS 143A.

*Quantity of flowers per spadix*.—Approximately 260.

*Spadix flower arrangement*.—Rotate.

*Spadix flower shape*.—Flattened; rotate.

*Spadix flower diameter*.—Approximately 2.0 mm.

*Spadix flower depth*.—Approximately 0.75 mm.

Reproductive organs:

*Androecium*.—Stamen quantity — 4. Filament — Length — Very short; approximately 0.1 mm long. Color — Light yellow-orange; R.H.S. color designations cannot be determined due to the minute nature of the filament. Anther — Anther shape — Narrow, oblong with a longitudinal slit forming two halves. Anther size — 0.5 mm long and 0.25 mm in diameter. Anther color — Yellow, nearest to RHS 11D. Pollen — Amount of pollen — Low to moderate. Pollen color — Light greyed-yellow, nearest to RHS 161D.

*Gynoecium*.—Pistil quantity — One. Length — 0.5 mm. Stigma — Shape — Club-shaped. Dimensions — Approximately 0.3 mm across and 0.15 mm tall. Color — White, nearest to RHS 155C.

*Style*.—Length — 0.35 mm. Color — Yellow-green; R.H.S. color designations cannot be determined due to the minute nature of the filament. Ovary — Color — Yellow-orange, nearest to RHS 14D.

SEED AND FRUIT

Seed production has not been observed.

COMPARISONS WITH THE PARENT

Plants of the new cultivar 'ARAANTRED5' differ from the seed parent, *Anthurium* 'K25' (not patented), in the following characteristics described in Table 1 below.

TABLE 1

| Characteristic | 'ARAANTRED5' | 'K25' |
|---|---|---|
| Leaf size. | Smaller than 'K25'. | Larger than 'ARAANTRED5'. |
| General coloration of mature foliage. | Darker green. | Lighter green. |
| Spathe shape. | Broad cordate; more rounded than 'K25'. | Cordate; narrower than 'ARAANTRED5'. |
| Aspect of the spathe. | Margins at the base of the spathe are revolute. | Margins at the base of the spathe are involute. |

Plants of the new cultivar 'ARAANTRED5' may be distinguished from the pollen parent, 'K20' (not patented), by the following combination of characteristics described in Table 2 below.

TABLE 2

| Characteristic | 'ARAANTRED5' | 'K20' |
|---|---|---|
| General coloration of mature foliage. | Darker green. | Lighter green. |
| Foliage size. | Smaller than 'K20'. | Larger than 'ARAANTRED5'. |
| Foliage apex. | Apiculate. | Narrowly apiculate. |
| Spathe length. | Shorter than those of 'K20'. | Longer than those of 'ARAANTRED5'. |

COMPARISONS WITH THE MOST SIMILAR VARIETY OF COMMON KNOWLEDGE

Plants of the new cultivar 'ARAANTRED5' differ from the commercial variety, *Anthurium* 'Red King' (U.S. Pat. No. 13,381), in the following characteristics described in Table 3 below.

TABLE 3

| Characteristic | 'ARAANTRED5' | 'Red King' |
|---|---|---|
| Growth habit. | More compact than 'Red King'. | Less compact than 'ARAANTRED5'. |
| Foliage size. | Smaller than 'Red King'. | Larger than 'ARAANTRED5'. |
| General coloration of the mature foliage. | Darker green. | Lighter green. |
| Thickness of the spathe. | Thicker than 'Red King'. | Thinner than 'ARAANTRED5'. |
| Spathe shape. | Broad cordate; more rounded than 'Red King'. | Cordate; narrower than 'ARAANTRED5'. |

That which is claimed is:

1. A new and distinct variety of *Anthurium* plant named 'ARAANTRED5', substantially as described and illustrated herein.

* * * * *